(12) United States Patent
Harima et al.

(10) Patent No.: US 8,273,370 B2
(45) Date of Patent: Sep. 25, 2012

(54) ADHESIVE PATCH

(75) Inventors: Jun Harima, Ibaraki (JP); Masakatsu Konno, Ibaraki (JP); Ryo Hashino, Ibaraki (JP); Akira Numata, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 238 days.

(21) Appl. No.: 12/548,550

(22) Filed: Aug. 27, 2009

(65) Prior Publication Data

US 2010/0055162 A1 Mar. 4, 2010

(30) Foreign Application Priority Data

Aug. 28, 2008 (JP) ................... 2008-219190

(51) Int. Cl.
*A61K 9/70* (2006.01)
*A61F 13/02* (2006.01)
(52) U.S. Cl. ...................... 424/449; 424/443
(58) Field of Classification Search .............. 424/449, 424/443
See application file for complete search history.

(56) References Cited

U.S. PATENT DOCUMENTS

| | | | |
|---|---|---|---|
| 5,591,447 A * | 1/1997 | Jensen | 424/443 |
| 6,495,229 B1 | 12/2002 | Carte et al. | |
| 2003/0064190 A1 | 4/2003 | Carte et al. | |
| 2005/0147654 A1 * | 7/2005 | Matloub et al. | 424/443 |
| 2007/0106195 A1 * | 5/2007 | Marcoux et al. | 602/57 |
| 2009/0092819 A1 | 4/2009 | Malik et al. | |

FOREIGN PATENT DOCUMENTS

| | | | |
|---|---|---|---|
| JP | 09-124462 | | 5/1997 |
| WO | 94/14062 | | 6/1994 |
| WO | WO94/14062 | * | 6/1994 |
| WO | 01/19306 | | 3/2001 |
| WO | 2007/109593 | | 9/2007 |
| WO | 2009/049008 | | 4/2009 |

OTHER PUBLICATIONS

European Search Report dated Dec. 11, 2009 in European Patent Application No. 09168756.

* cited by examiner

*Primary Examiner* — Anoop Singh
*Assistant Examiner* — Anna Falkowitz
(74) *Attorney, Agent, or Firm* — Wenderoth, Lind & Ponack, L.L.P.

(57) ABSTRACT

An adhesive patch has a support and an adhesive layer formed on at least one surface of the support. The adhesive patch has a peripheral part and a central part 21. The adhesive layer has voids localized in the peripheral part, with the adhesive layer in the central part being substantially free of voids. The peripheral part preferably contains voids at 2.0-100 voids/ $mm^3$ on average. Since time-course changes of adhesive layer components such as additives are reduced, the adhesive patch is highly resistant to detachment from the skin, the components do not easily protrude from the edge of the adhesive patch during preservation in a package, adhesion to the inner surface of the package is suppressed, the adhesive patch can be easily removed from the package and edge lifting by cold flow is suppressed during adhesion to the skin.

10 Claims, 6 Drawing Sheets

ADHESIVE PATCH

TECHNICAL FIELD

The present invention relates to an adhesive patch comprising a support and an adhesive layer formed on at least one surface of the support.

BACKGROUND OF THE INVENTION

In recent years, various adhesive patches and adhesive preparations have been developed. Adhesive patch and adhesive preparation are highly superior from the aspects of wound protection and/or continuous transdermal administration of a drug.

In general, an adhesive patch comprises a support made of a cloth, a plastic film and the like and an adhesive layer laminated on the support, and is generally provided with a release liner laminated on the adhesive layer and in a package made of a resin film and the like.

In such adhesive patch, when the adhesive layer becomes thick, the edge of the adhesive patch is easily rubbed against clothes and the like and turned up, as well as the components of the adhesive layer protrude from the edge of the adhesive patch, i.e., cold flow, thus posing problems during adhesion to the skin.

Cold flow occurs depending on the property of an adhesive. It often occurs when, in particular, an adhesive patch is under a load for a long time, namely, when an adhesive patch is contained in a package and stored for a long period and the like.

Adverse influences of cold flow include, for example, degraded performance of taking out of an adhesive patch from a package, which is caused by adhesion of protruded adhesive layer components to the inside of the package, edge lifting and staining of adhesive patch during adhesion to the skin, a lower effect including a lower medicinal effect of the adhesive patch and the like. Therefore, an adhesive patch desirably has an edge which is not easily rubbed against clothes and does not permit easy cold flow, and has an adhesive layer retaining the original shape.

To balance prevention of skin irritation (improvement of moisture permeability) and improvement of transdermal absorbability of the drug, which are contradictory for an adhesive preparation containing a transdermally absorbable drug, JP-A-9-124462 discloses an adhesive patch and an adhesive preparation that achieve the balance thereof by disposing a void forming member such as a non-woven fabric and the like in an adhesive layer to form voids in the adhesive layer.

However, the voids formed in the adhesive layer described in JP-A-9-124462 are sequentially present in the flat plane direction of the adhesive patch and reach the edge of the adhesive patch, and therefore, adhesive layer components such as additives and the like may be affected by the environment outside the adhesive patch via the voids. In the adhesive patch described in patent document 1, therefore, a new consideration to suppress volatilization and decomposition of adhesive layer components and improve stability of the adhesive layer components over time is necessary.

In addition, the constitution disclosed in JP-A-9-124462, wherein voids are sequentially present in the flat plane direction of the adhesive patch and reach the edge of the adhesive patch, aims to balance improvement of moisture permeability and improvement of transdermal absorbability of drug, and therefore, is not effective for the prevention of the aforementioned cold flow. The constitution disclosed in JP-A-9-124462 is still associated with the possible problems mentioned above, i.e., protrusion of adhesive layer components from the edge of an adhesive patch, which is particularly frequently observed during long-term preservation of an adhesive patch under a load for a long time and the like, degraded take out performance of an adhesive patch from a package due to adhesion of protruded adhesive layer components to the inside of the package, edge lifting of an adhesive patch during adhesion to the skin and the like.

SUMMARY OF THE INVENTION

The present invention has been made in view of such situation and the problem to be solved thereby is the provision of an adhesive patch which reduces changes of adhesive layer components such as additive and the like over time and is highly resistant to detachment from the skin surface, wherein the adhesive layer components do not easily protrude from the edge of the adhesive patch during preservation in a package, adhesion of the adhesive patch to an inner surface of the package is suppressed, the adhesive patch can be easily taken out from the package, and edge lifting of the adhesive patch caused by cold flow is suppressed during adhesion to the skin.

The present inventors conducted intensive studies and found that the aforementioned problem can be resolved by not forming voids that are sequentially present in the flat plane direction of the adhesive patch and reach the edge of the adhesive patch but by forming voids localized in the peripheral part of an adhesive layer, which resulted in the completion of the present invention.

Accordingly, the present invention provides the following.

[1] An adhesive patch comprising a support and an adhesive layer formed on at least one surface of the support, wherein the adhesive patch has a peripheral part and a central part, the adhesive layer has voids, wherein the aforementioned adhesive layer in the aforementioned central part is substantially free of the aforementioned voids, and the voids in the adhesive layer are localized in the peripheral part.

[2] The adhesive patch of the aforementioned [1], wherein the aforementioned adhesive layer in the aforementioned peripheral part has the aforementioned voids at a rate of 2.0-100 voids/mm$^3$ on average.

[3] The adhesive patch of the aforementioned [1], wherein the thickness of the peripheral part of the adhesive layer is smaller than that of the central part of the adhesive layer.

[4] The adhesive patch of the aforementioned [1], wherein the support is a laminate of a porous material and a resin film, and the adhesive layer is laminated on the porous material side of the laminate.

[5] The adhesive patch of the aforementioned [1], wherein the flat plane shape of the peripheral part has a band-like portion having a width of 0.29-3.5 mm.

[6] The adhesive patch of the aforementioned [1], wherein the central part of the adhesive layer has a thickness of not less than 50 μm.

[7] The adhesive patch of the aforementioned [1], wherein the central part of the adhesive layer has a thickness of 100-4000 μm, and the peripheral part of the adhesive layer has a thickness of 1.5-300 μl which is smaller than the thickness of the central part of the adhesive layer.

[8] The adhesive patch of the aforementioned [1], wherein the adhesive layer further comprises a drug.

[9] The adhesive patch of the aforementioned [1], further comprising a release liner laminated on the adhesive layer.

The adhesive patch of the present invention has voids localized in the peripheral part of the adhesive layer, the central part of the adhesive layer is substantially free of voids, and the adhesive layer has a particular number of voids in the peripheral part. Hence, the voids can trap adhesive layer components such as additives and the like, which have cold-flowed from the central part of the adhesive layer. Consequently, when the adhesive patch of the present invention is packed and preserved in a package, protrusion of the adhesive layer components such as additives and the like from the edge of the adhesive patch does not occur easily, and adhesion of the adhesive patch to an inner surface of the package can be suppressed. According to the present invention, moreover, the adhesive patch can be taken out easily from the package, users' hands less often become sticky during handling of the adhesive patch, edge lifting of the adhesive patch, which is caused by cold flow during adhesion to the skin, is also suppressed, and the adhesive patch can be used comfortably.

Moreover, according to the adhesive patch of the present invention, the voids in the peripheral part of the adhesive layer at least partly divide the central part of the adhesive layer from the edge of the adhesive layer, and therefore, the influence on adhesive layer components such as additives and the like from the environment outside the adhesive patch can be reduced. As a result, time-course changes of the adhesive layer components such as additives and the like over time can be reduced.

Figure 1A:
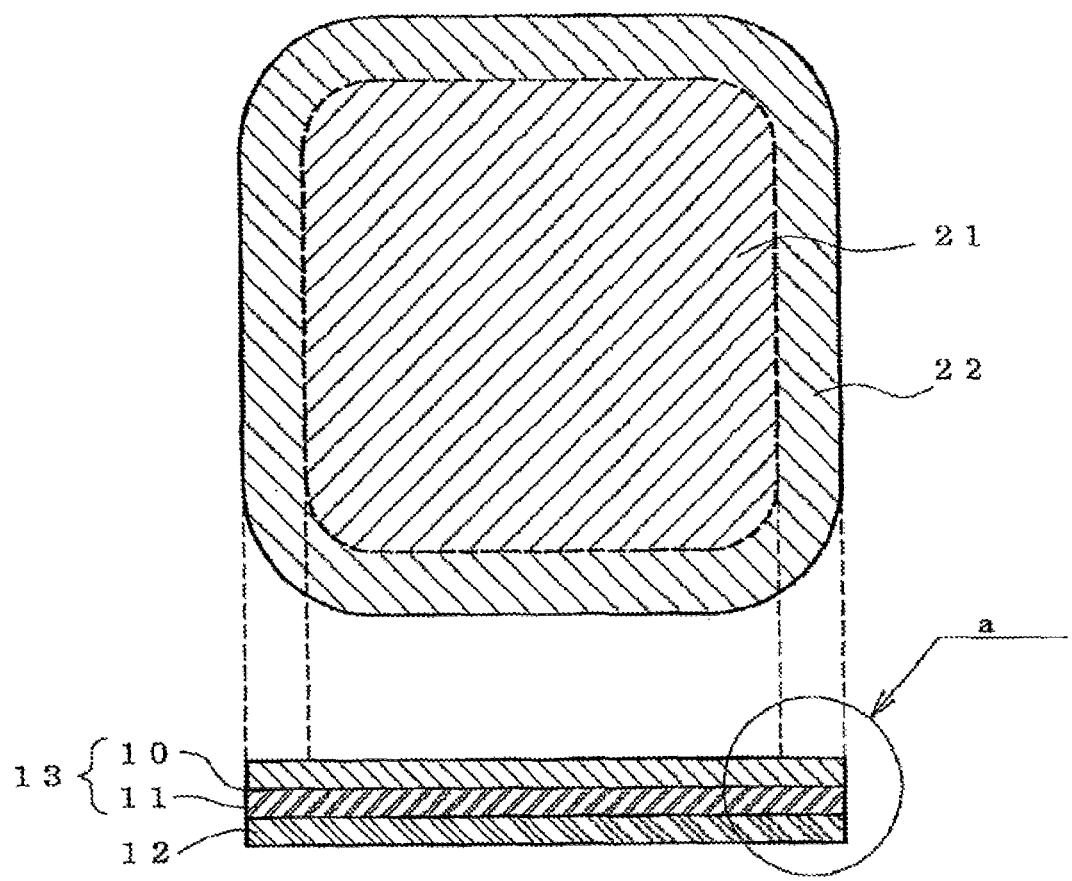
FIG. 1A is a schematic plane view showing the shape of one embodiment of the adhesive patch of the present invention.

REFERENCE CHARACTERS 10 support
11 adhesive layer
12 release liner
13 adhesive patch main part
21 central part
22 peripheral part
23 intermediate part
31 void (air bubble)
41 package
d1 maximum diameter of void in peripheral part, in direction perpendicular to main surface of adhesive patch
d2 maximum diameter of void in peripheral part, in direction perpendicular to thickness direction of adhesive patch
60 package
61 V-shaped notch
62 adhesive patch

DESCRIPTION OF THE INVENTION

In the present specification, the adhesive patch is a concept embracing not only those free of a drug but also adhesive preparation comprising a drug. Those comprising a drug are sometimes particularly referred to as an adhesive preparation.

The present invention is explained in detail in the following by referring to the attached drawings. In the drawings, the dimensional size ratios of elements used to explicitly indicate each element are different from actual ratios.

The adhesive patch of the present invention has a substantially flat plane form. The flat shape of the adhesive patch of the present invention includes, but is not limited to, for example, an approximate rectangle, a polygon such as a triangle, a pentagon and the like, or a shape defined by approximately straight lines, a shape defined by curved lines such as an ellipse, a circular shape and the like, a combination thereof and the like. The size of the adhesive patch is not limited, and can be selected as appropriate according to the use, the size of the application site and the like of the adhesive patch. For example, when the adhesive patch has an about square or an about rectangular shape, the length of one side thereof is generally 30-90 mm, and the length of other side is generally 30-90 mm.

Figure 1B:
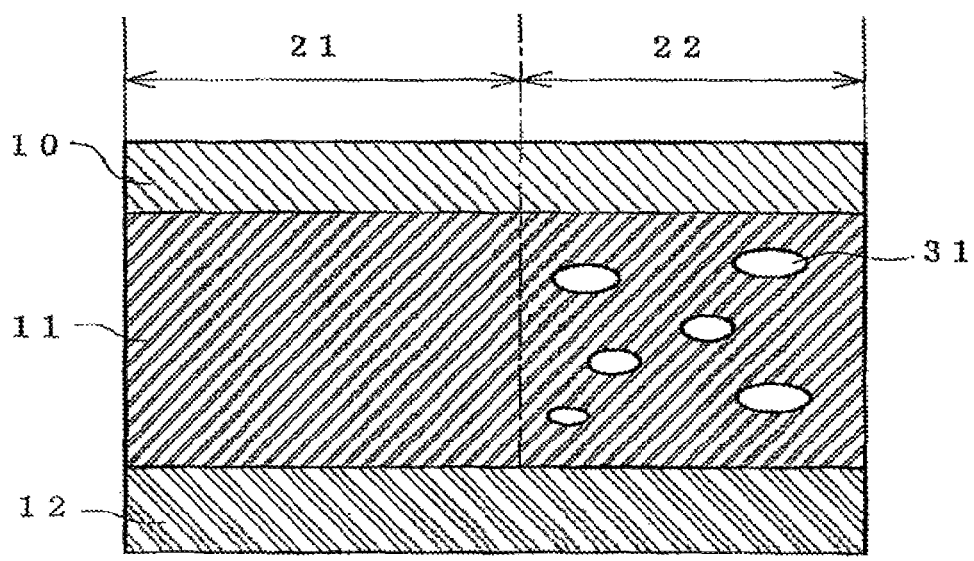
FIG. 1B is a schematic sectional view showing part a of FIG. 1A.

FIGS. 1A and 1B are schematic views showing one embodiment of the adhesive patch of the present invention. The adhesive patch of the present invention comprises an adhesive patch main part 13 comprising a support 10 and an adhesive layer 11 formed on at least one surface of the support 10, and may have a release liner 12 laminated on an adhesive surface of the adhesive layer 11 of the adhesive patch main part 13 so as to protect the adhesive surface until adhesion to the skin. The adhesive patch of the present invention is characterized in that it has a central part 21 and a peripheral part 22 that is located outside the central part 21 and includes the edge of the adhesive patch, the aforementioned adhesive layer 11 has a void 31, which is localized in the peripheral part 22 of the adhesive layer 11, and the adhesive layer 11 in the central part 21 is substantially free of voids. That is, in the present invention, the peripheral part 22 is located outside the central part 21, which is a region in the adhesive patch main part 13 containing the edge of the adhesive patch, where voids 31 are localized in the adhesive layer 11.

The voids in the adhesive layer, which are localized in the peripheral part, contain air bubbles in the adhesive layer.

While the sizes and shapes of the voids are not particularly limited, they generally have a quasi-spherical or flattened spherical shape.

As shown in FIG. 1B, the adhesive patch of the present invention comprises voids localized in the peripheral part of the adhesive layer. Therefore, the voids can trap adhesive layer components such as additives and the like, which have cold-flowed from the central part of the adhesive layer. Consequently, when the adhesive patch of the present invention is packed and preserved in a package, protrusion of the adhesive layer components such as additives and the like from the edge of the adhesive patch does not occur easily, and adhesion of the adhesive patch to an inner surface of the package can be suppressed. According to the present invention, moreover, the adhesive patch can be taken out easily from the package, a users' hands less often become sticky during handling of the adhesive patch, edge lifting of the adhesive patch, which is caused by cold flow during adhesion to the skin, is also suppressed, and the adhesive patch can be used comfortably. Moreover, according to the adhesive patch of the present invention, the voids at least partly divide the central part of the adhesive layer from the edge of the adhesive layer, and therefore, the influence on adhesive layer components such as additives and the like from the environment outside the adhesive patch can be reduced. As a result, time-course changes of the adhesive layer components such as additive and the like can be reduced.

Figure 2A:
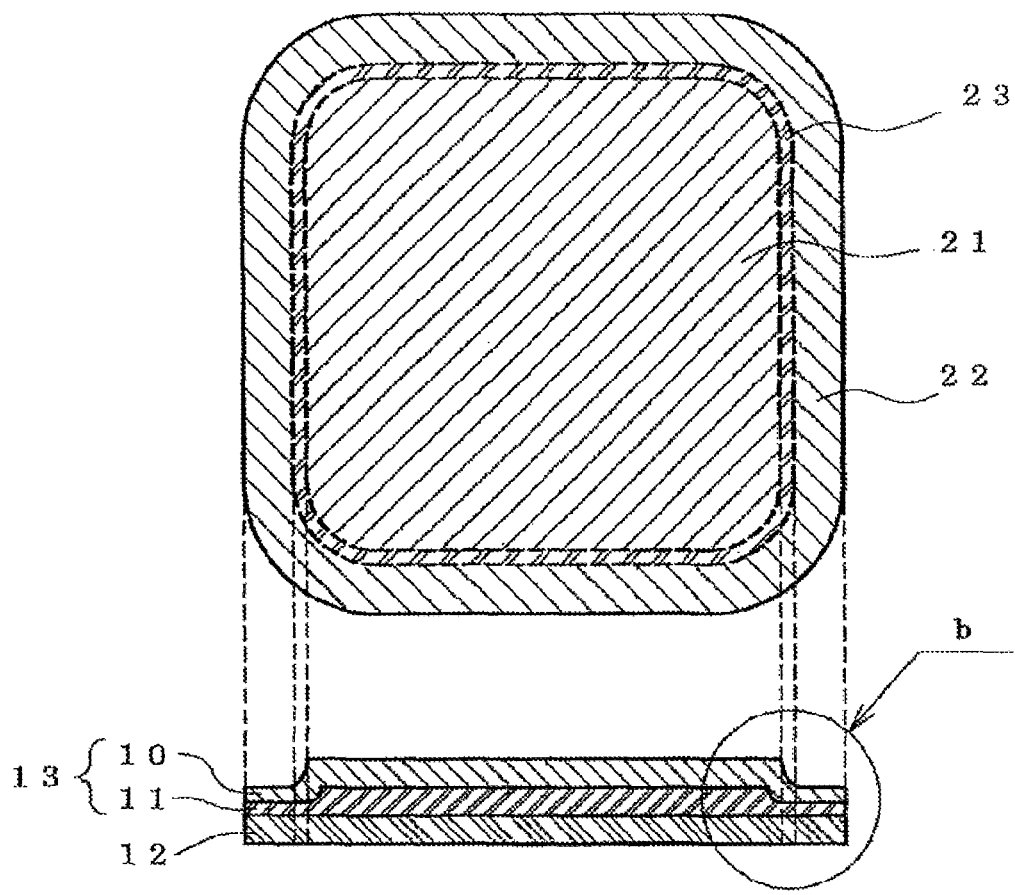
FIG. 2A is a schematic plane view showing a preferable embodiment of the adhesive patch of the present invention.
Figure 2B:
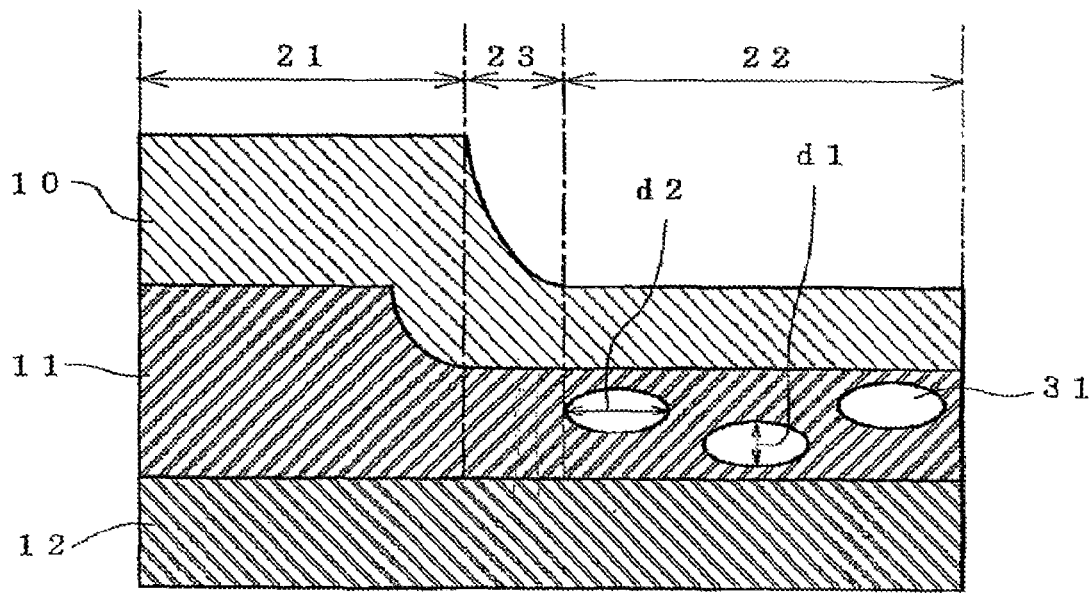
FIG. 2B is a schematic sectional view showing part b of FIG. 2A.

The maximum diameter of voids in the peripheral part, which is in direction perpendicular to main surface of adhesive patch, as shown by d1 in FIG. 2B, is preferably ½ or more, more preferably ⅔ or more, of the thickness of the peripheral part of the adhesive layer. The voids preferably is penetrate the adhesive patch from the release liner to the support in the peripheral part of the adhesive layer (i.e., the aforementioned maximum diameter of the void is the same as the thickness of the peripheral part of the adhesive layer). This is because such voids can effectively trap adhesive layer components that may flow out, whereby protrusion or outflow of the adhesive layer components from the edge of the adhesive patch (edge of the adhesive layer) can be more effectively suppressed.

FIGS. 2A and 2B are schematic diagrams showing one embodiment of the adhesive patch of the present invention. The same number symbols in FIGS. 2A, 2B as in FIG. 1A, 1B show the corresponding elements in FIG. 1, and the region of adhesive patch main part 13 between the central part 21 and the peripheral part 22 is referred to as an intermediate part 23. In the embodiment shown in FIGS. 2A and 2B, the thickness of the peripheral part 22 of the adhesive layer 11 is smaller than that of the central part 21 of the adhesive layer 11, whereby the voids can more effectively trap adhesive layer components, which tend to outflow from the adhesive layer, than in the embodiment shown in FIGS. 1A and 1B, even when the maximum diameter of voids in the peripheral part, which is in the direction perpendicular to main surface of adhesive patch, is the same. Thus, the above-mentioned effect of the present invention can be more remarkably afforded.

Figure 3:
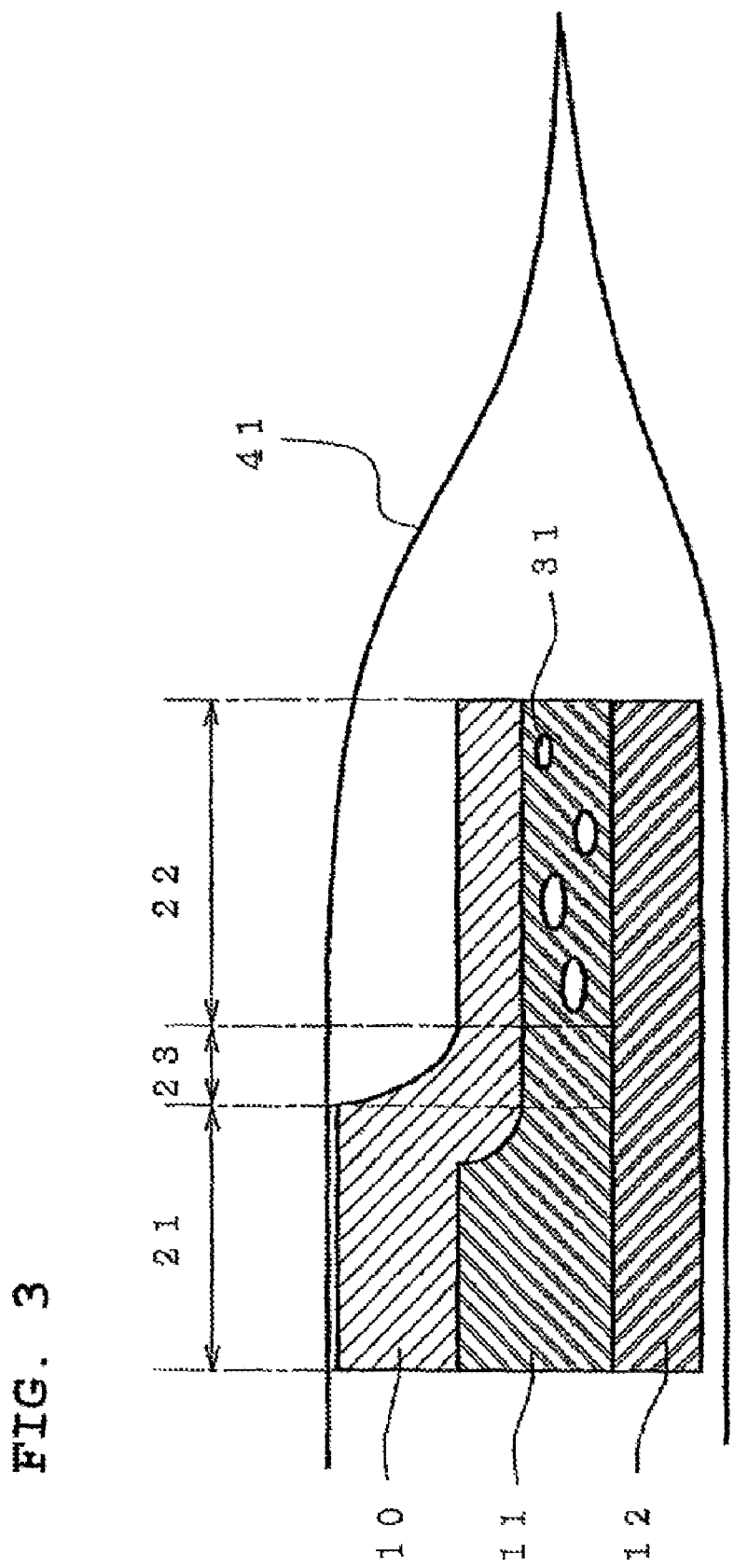
FIG. 3 is a schematic sectional view showing one preferable embodiment of the adhesive patch of the present invention contained in a package and which shows a characteristic shape.

Moreover, in an embodiment where the thickness of the peripheral part of the adhesive layer is smaller than that of the central part of the adhesive layer, as shown in FIG. 3, when an adhesive patch is packed in a package 41, the central part 21 functions to support the package 41. As a result, the frequency of contact of the edge of the adhesive patch against an inner surface of the package 41 decreases and, even when the adhesive layer components protrude or flow out from the edge of the adhesive patch, adhesion of the adhesive patch to the package 41 is suppressed, and the adhesive patch can be easily taken out from package 41.

Furthermore, in an embodiment where the thickness of the peripheral part of the adhesive layer is smaller than that of the central part of the adhesive layer, since the thickness of the adhesive patch main part is greater in the central part than in the peripheral part, such central part can fulfill the function to hold up clothing after adhesion of the adhesive preparation to the skin. As a result, the frequency of rubbing of the edge of the adhesive patch against clothing can be reduced. Hence, the adhesive patch of the present invention is highly resistant to the detachment from the skin surface.

Now the shape and size of the adhesive patch main part of the present invention, particularly a characteristic shape thereof, are more specifically explained. The shape of the flat plane of the peripheral part preferably has a band-like part having a width of 0.29-5 mm, more preferably 0.29-3.5 mm. By setting the width of the peripheral part to fall within the above-mentioned range, protrusion or outflow of the adhesive layer component from the edge of the adhesive patch can be more effectively suppressed, and the peripheral part of the adhesive layer does not become too large. Thus, a decrease in the adhesiveness of the peripheral part of the adhesive patch can be prevented more effectively. To sufficiently achieve the effect of the present invention, the adhesive patch preferably has such a band-like part in each peripheral part.

The thickness of the central part of the adhesive layer is, for example, 50-5000 μm, preferably 100-4000 μm. When it is smaller than 100 μm, the adhesiveness may decrease and when it exceeds 4000 μm, the shape of the adhesive layer cannot be easily retained and, depending on the adhesive layer components, the adhesive layer components may strikingly protrude from the edge of the adhesive patch.

The thickness of the peripheral part of the adhesive layer is preferably not more than 300 μm, more preferably not more than 50 μm, in consideration of the ratio of the maximum diameter of void in peripheral part, which is in the direction perpendicular to the main surface of the adhesive patch, relative to the thickness of the peripheral part of the adhesive patch, for effective trapping of the adhesive layer components. The thickness of the peripheral part of the adhesive layer is also preferably not less than 1.5 μm so as to ensure the necessary skin adhesiveness. The difference in the thickness of the adhesive patch main part in the central part and the thickness of the adhesive patch main part in the peripheral part is preferably 20-2000 μm so as to hold up package or clothing in the central part and reduce the frequency of rubbing of the edge of the adhesive patch main part against package or clothes. Since the thickness of the support is almost constant from the peripheral part to the central part, the difference in the thickness of the central part of the adhesive layer and the thickness of the peripheral part of the adhesive layer is the same as mentioned above.

The adhesive patch of the present invention affords an effect based on localization of voids in the peripheral part of the adhesive layer, and the central part of the adhesive layer is preferably substantially free of voids. In the present specification, "the central part of the adhesive layer is substantially free of voids" means that the central part of the adhesive layer does not contain voids, or if it does, contains not more than 1.0 void/mm$^3$ on average, and "voids in the adhesive layer are localized in the peripheral part" means that the peripheral part of the adhesive layer contains voids at a rate of at least 2.0 voids/mm$^3$ on average, and therefore, the average number of voids in the peripheral part of the adhesive layer is at least twice that of the central part.

The adhesive patch of the present invention is characterized in that the peripheral part of the adhesive layer preferably contains voids at 2.0-100 voids/mm$^3$, more preferably 2.0-10 voids/mm$^3$, on average. When the average number of voids in the peripheral part of the adhesive layer is higher than 100 voids/mm$^3$, the proportion of an adhesive in the adhesive layer becomes small, skin adhesiveness may decrease in the peripheral part of the adhesive patch, and when it is less than 2.0 voids/mm$^3$, the aforementioned effect of the present invention cannot be achieved sufficiently.

In the present invention, the average number of voids contained in the adhesive layer (the average number of voids contained per unit volume of the adhesive layer) is a value obtained by producing a section perpendicular to the main surface of the adhesive patch with a freezing microtome at at least 4 points of the adhesive patch, imaging the section with an FE-SEM (Hitachi, field-emission-type scanning electron microscope S-4800) at 50- to 1000-power, and reading the gauge scale.

More specifically, the average number of voids contained in the adhesive layer is obtained by cutting both the central part and the peripheral part of an approximately rectangle or approximately square adhesive patch in at least one point of each side (at least 4 points in total of adhesive patch), in the direction perpendicular to each side for at least 3000 μm, with a freezing microtome, imaging each section, counting, based on the gauge scale, voids having a diameter (maximum diameter) of not less than 1 μm in the thickness direction of an adhesive patch as shown in FIG. 2, d2 in a 700 μm×600 μm section of each image and calculating the number of voids per 1 mm$^3$ adhesive layer.

Figure 4:
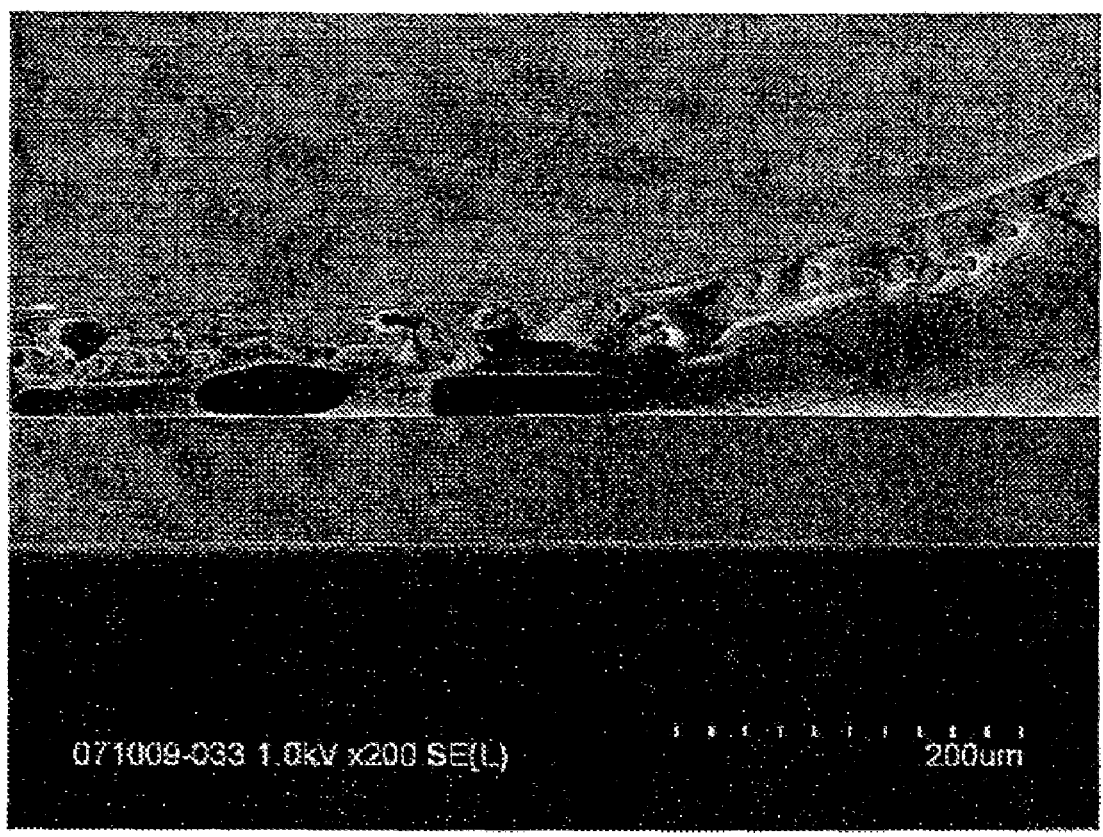
FIG. 4 is an FE-SEM image of the adhesive patch of the present invention wherein the peripheral part of the adhesive layer has a thickness smaller than that of the central part of the adhesive layer, which was taken along the section perpendicular to the main surface of the adhesive patch at 200-power while focusing on the adhesive layer from the peripheral part to the intermediate part.
Figure 5A:
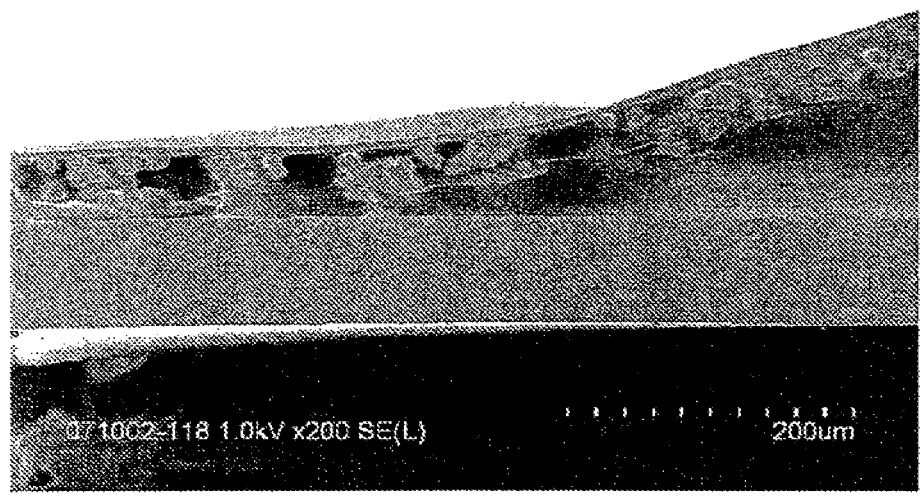
FIG. 5A is an FE-SEM image of the adhesive patch of the present invention wherein the peripheral part of the adhesive layer has a thickness smaller than that of the central part of the adhesive layer, which was taken along the section perpendicular to the main surface of the adhesive patch at 200-power while focusing on the adhesive layer from the peripheral part to the intermediate part.

FIG. 4 and FIG. 5A show an FE-SEM image of the adhesive patch of the present invention wherein the peripheral part of the adhesive layer has a thickness smaller than that of the central part of the adhesive layer, which was taken along the section perpendicular to the main surface of the adhesive patch at 200-power while focusing on the adhesive layer from the peripheral part to the intermediate part. FIG. 4 and FIG. 5A show that the adhesive layer is placed on a release liner, and the voids in the adhesive layer are localized in the peripheral part (left side).

As shown in FIG. 4 and FIG. 5A, the shape of the voids in the peripheral part of the adhesive layer of the adhesive patch of the present invention varies from an independent void, one or more kinds of voids which are partly connected and the like. The maximum diameter of voids in the direction perpendicular to the thickness direction of the adhesive patch as shown in FIG. 2B, d2 is preferably 5-300 μm, which can be adjusted by a production method including introduction of the below-mentioned air bubbles. The maximum diameter of voids in the direction perpendicular to the main surface of the adhesive patch as shown in FIG. 2B, d1 is preferably ½ to 1-fold of the diameter (maximum diameter) of voids in the direction perpendicular to the thickness direction of the adhesive patch.

Thus, the shape of the void may vary depending on the voids, and the size of the voids can change. For the measurement of the average number of voids contained in the adhesive layer in the present invention, even when one or more kinds of voids are partly connected, as long as they are not observed as being completely divided, the voids are counted as one. The measurement was performed only for the voids having a diameter (maximum diameter) of not less than 1 μm in the thickness direction of an adhesive patch, in the observed section, excluding voids having a diameter of less than 1 μm.

Since the average number of voids contained in the adhesive layer in the present specification is not obtained based on the volume of voids, even if two adhesive layers have the same average number of voids, the total volume of the voids may be different.

While the support of the above-mentioned adhesive patch is not particularly limited, a support which is substantially drug impermeable, namely, a support which does not permit an active ingredient, an additive and the like in the adhesive layer to pass through the support and be lost from the back face to cause a decreased content is preferable.

In the present invention, the support is preferably a laminate of a porous material and a resin film, wherein the adhesive layer is laminated on the porous material of the laminate. A porous material has concaves and convexes on the surface and such unevenness is considered to suppress movement or disappearance of voids (air bubbles) possibly contained in the adhesive layer. Therefore, using the porous material, outflow and protrusion of adhesive layer components can be suppressed more effectively. When a porous material is used, since it contains voids (air bubbles), it is considered that the voids move to the adhesive layer of the peripheral part of the adhesive patch, and are fused with air bubbles in the adhesive layer to possibly form greater air bubbles in the peripheral part, whereby the effect of the present invention is enhanced. It is preferable that the voids (air bubbles) in the peripheral part of the adhesive layer of the adhesive patch of the present invention reach the surface of the porous material, and more preferably, it reaches the surface of the adhesive layer side of the resin film.

Examples of the porous material include porous film and sheet. When the sheet has a thickness of not less than 200 μm, a porous film is preferable. The aforementioned porous film may be a single layer film or a laminate film, and one having an anchoring ability to suppress movement of the adhesive layer to the porous material can be preferably used. Specific examples include paper, woven fabric, non-woven fabric, knitted fabric, mechanically perforation-treated film and metal foil, laminates thereof and the like. Of these, paper, woven fabric, non-woven fabric, and laminates thereof are particularly preferable from the aspects of handling performance and the like, and non-woven fabric is especially preferable.

The resin film may be a single layer film or a laminate film, with preference given to a non-porous film composed of a resin impermeable to active ingredients.

The porous film and resin film may be made of similar materials or different materials. These films can be laminated according to a known method. They may contain various additives such as antioxidants, pigments, antistatic agents and the like as appropriate as long as the effect of the invention and effect of the adhesive patch are not impaired. In addition, the surface thereof may be subjected to a corona discharge treatment, an ultraviolet irradiation treatment or the like.

Examples of the material of such porous film and resin film constituting the support include polyester, nylon, Saran (registered trade mark of Asahi Kasei Corporation or Dow Chemical Company, USA), polyethylene, polypropylene, poly(vinyl chloride), ethylene-ethyl acrylate copolymer, poly (tetrafluoroethylene), Surlyn (registered trade mark of DuPont, USA), combinations thereof and the like.

Such resin films suppress permeation of adhesive layer components through the back face of the support to reduce the content thereof. In addition, when the adhesive layer contains a drug, they are preferably used to achieve an effect of what is called an occlusive dressing technique (ODT).

When the below-mentioned production method of the adhesive patch of the present invention characterized by pressing and heating the area corresponding to the peripheral part of the adhesive patch main part is employed, in order to form the intermediate part in the adhesive patch main part, the materials of the porous film and the resin film constituting the support are preferably thermoplastic resins, for example, polyester, polypropylene, polyethylene and the like, and particularly preferably polyester, for example, poly(ethylene terephthalate), since they become soft by heating, are deformed thereafter, and maintain the deformed shape after cooling.

The thickness of the porous film is preferably within the range of 10-100 μm so as to afford improved anchoring ability, flexibility of the entire adhesive patch, adhesion operability and the like. When a woven fabric or non-woven fabric is used as a porous film, the basis weight thereof is preferably 5-50 g/m$^2$, more preferably 10-30 g/m$^2$, to secure air bubbles having an effective size and achieve anchoring property.

In the present invention, the thickness of the porous film is measured by staining an adhesive patch with an aqueous ruthenium acid solution, imaging a section produced with a freezing microtome with an FE-SEM (Hitachi, S-4800) at 50- to 1000-power, and reading the gauge scale. In this case, concaves and convexes are present on the surface of the porous film. In a sectional image, 10 convexes are selected at random, and an average of the thickness of the porous film at the convexes is calculated and taken as the thickness of the porous film.

In the present invention, the basis weight of the porous film is determined by multiplying the thickness of the above-mentioned porous film by the specific gravity (apparent specific gravity) of the porous film and calculating the weight of the porous film per unit area.

While the thickness of the resin film is not particularly limited, it is preferably 1-100 μm. When it is less than 1 μm, impermeability to drug and the like may be impaired, and such thickness is also unpreferable for formation of an intermediate part. When it exceeds 100 μm, the rigidity of the resin film can possibly develop an uncomfortable feeling during adhesion of the skin. Moreover, when it exceeds 100 and the below-mentioned production method characterized by pressing and heating the area corresponding to the peripheral part of the adhesive patch main part is employed, a shape wherein the thickness of the peripheral part of the adhesive layer is smaller than that of the central part of the adhesive layer may not be secured. In the present invention, the thickness of the resin film is measured in the same manner as for the above-mentioned porous film.

Thus, a desirable support in the present invention is a laminate film of a polyester film with 1-100 μm thickness (preferably, poly(ethylene terephthalate) film) and a non-woven fabric made of polyester (preferably, poly(ethylene terephthalate)) having a basis weight of 10-30 g/m$^2$.

In consideration of the skin-following ability and comfortableness during application of an adhesive patch, the total thickness of the support is preferably 5-200 μm.

Now, a production method of a composition for forming the adhesive layer (composition for adhesive layer formation) and the amounts of components constituting the adhesive layer are explained. The amount of each component described in the following for the preparation of the composition for adhesive layer formation is a ratio in wt % of the amount of each component relative to the amount of whole components except solvent (organic solvent).

In the region corresponding to the central part of the adhesive patch, the adhesive layer can be formed by mixing an adhesive with components such as a drug, a tackifier, an organic liquid component and the like as necessary in the presence of a solvent to give a composition for formation of the central part of an adhesive layer, forming layers thereof by a method such as coating and the like, and drying the layers. The adhesive layer is preferably a hydrophobic adhesive layer in view of adhesion to the skin, and therefore, an anhydrous adhesive layer is preferable. From such aspect, the aforementioned solvent is preferably an organic solvent.

The adhesive layer in the region corresponding to the peripheral part of the adhesive patch can be formed by preparing a composition for formation of a peripheral part adhesive layer, forming a layer by a method such as coating and the like, and drying the layer. By introducing air bubbles into the composition before forming the layer, voids can be formed. The composition for formation of a peripheral part adhesive layer may be the same as or different from the composition for formation of the central part adhesive layer in the components and amounts thereof. To form air bubbles and maintain the bubbles for a given time, the viscosity is preferably 5-50 Pa·s.

While the organic solvent is not limited, one having compatibility with the aforementioned respective components constituting the adhesive layer and easily volatilizable during a drying process is preferable. In addition, a solvent that can form air bubbles in a composition for formation of a peripheral part adhesive layer and maintain the bubbles for a given time is preferable. Examples of the organic solvent include aromatic hydrocarbons such as toluene, xylene and the like, aliphatic hydrocarbons such as hexane and the like, esters such as ethyl acetate and the like, alcohols such as ethanol and the like, ethers such as diethyl ether, tetrahydrofuran, etc. and the like. These may be used alone or in a mixture of two or more kinds thereof in combination.

The aforementioned drying may be performed by air-drying, or according to a known method using a dryer, hot air, far-infrared radiation and the like.

While the method of mixing the aforementioned respective components is not limited, examples thereof include kneading machines such as a kneader, a planetary mixer and the like, dispersion machines such as homogenizer and the like, stirring machines such as propeller-type blade stirring machines, etc. and the like. These can be used alone or in a combination of two or more kinds thereof.

While the adhesive constituting the adhesive layer is not particularly limited, examples thereof include acrylic-based adhesives comprising acrylic-based polymer; styrene-diene-styrene block copolymers (e.g., styrene-isoprene-styrene block copolymer, styrene-butadiene-styrene block copolymer, etc.); rubber-based adhesives such as polyisoprene, polyisobutylene, polybutadiene and the like; silicone-based adhesives such as silicone rubber, dimethylsiloxane-based, diphenylsiloxane-based and the like; vinyl ether-based adhesives such as poly(vinyl methyl ether), poly(vinyl ethyl ether), poly(vinyl isobutyl ether) and the like; vinyl ester-based adhesives such as vinyl acetate-ethylene copolymer and the like; polyester-based adhesives comprising carboxylic acid component such as dimethyl terephthalate, dimethyl isophthalate, dimethyl phthalate and the like, and polyvalent alcohol components such as ethylene glycol, etc. and the like.

The adhesive layer may be a cross-linked adhesive layer obtained by a cross-linking treatment or a non-cross-linked adhesive layer obtained without a cross-linking treatment. Here, the cross-linking treatment refers to a known treatment applied to the adhesive layer so as to simultaneously achieve sufficient maintenance of skin adhesiveness of the adhesive patch, and suppression of skin irritation to a low level, which is caused by stretching the skin and physically scraping the stratum corneum of the skin to peel off the adhesive patch from the skin surface. Examples of the cross-linking treatment include a chemical crosslinking treatment, a treatment for ion cross-linking, and a physical crosslinking treatment using electron beam, ultraviolet light and the like. Examples of the crosslinking agent include metal salts such as zinc acetate and the like, an epoxy compound, an amide compound, an amine compound, acid anhydride, peroxide, an isocyanate compound and the like.

When the adhesive layer is a non-cross-linked adhesive layer, adhesive layer components tend to protrude or outflow from the edge of the adhesive patch. Even when the adhesive layer is a non-cross-linked adhesive layer, the adhesive patch of the present invention can effectively suppress protrusion and outflow of the adhesive layer components, and is particularly advantageous in such case.

Similarly, when the adhesive layer is the adhesive layer comprising a rubber-based adhesive, adhesive layer components tend to protrude or outflow from the edge of the adhesive patch, and the adhesive patch of the present invention is particularly advantageous in such case.

To achieve appropriate adhesive force and dissolution property of drugs, a rubber-based adhesive is a mixture of the same component or different components having different average molecular weights. To explain with polyisobutylene as an example, a mixture of high molecular weight polyisobutylene having a viscosity average molecular weight of 1,800,000-5,500,000, medium molecular weight polyisobutylene having a viscosity average molecular weight of 40,000-85,000 and, where necessary, lower molecular weight polyisobutylene is preferable. The viscosity average molecular weight in the present invention is determined by calculating a Staudinger index ($J_0$) according to the Schulz-Blaschke equation from the flow time of capillary of Ubbelohde viscometer at 20° C., and from the following formula using the obtained $J_o$ value:

$$J_0 = \eta_{sp}/\{c(1+0.31\eta_{sp})\} \text{ (Schulz-Blaschke equation)}$$

$\eta_{sp} = t/t_0 - 1$
t: flow time of solution (by Hagenbach-couette correction equation)
$t_0$: flow time of solvent (by Hagenbach-couette correction equation)
c: concentration of solution (g/cm$^3$)
$J_0 = 3.06 \times 10^{-2} \overline{M}v^{0.65}$
$\overline{M}v$: viscosity average molecular weight Here, it is preferable to contain high molecular weight polyisobutylene in a proportion of 10-80 wt %, preferably 10-50 wt %, medium molecular weight polyisobutylene in a proportion of 0-90 wt, preferably 10-80 wt %, and low molecular weight polyisobutylene in a proportion of 0-80 wt %, preferably 0-60 wt %. A generally obtained adhesive layer becomes stiff when the proportion of a high molecular weight component increases, and soft when the proportion of a low molecular weight component increases.

To confer an adequate adhesiveness to the adhesive layer, for example, a tackifier such as rosin-based resin, polyterpene resin, chroman-indene resin, petroleum-based resin, terpene-phenol resin, xylene resin and the like may be added. These may be used alone or in a mixture of two or more kinds thereof. Examples of the aforementioned petroleum-based resin include aliphatic series (C5 series) petroleum resin, aromatic series (C9 series) petroleum resin, copolymer series (C5-C9 series) petroleum resin and alicyclic saturated hydrocarbon resin obtained by partially or completely hydrogenating aromatic series (C9 series) petroleum resin. As the alicyclic saturated hydrocarbon resin, one having a softening point (ring and ball method) of 90-150° C. is preferable. While the amount of the tackifier is not limited, it is, for example, 10-40 wt % so as to impart appropriate adhesiveness and prevent saturation of the effect of a tackifier due to an increased amount thereof.

When desired, the adhesive patch of the present invention can contain a drug in the adhesive layer, whereby an adhesive preparation containing a drug can be provided. The drug here is not particularly limited, and a transdermally absorbable drug that can be administered to mammals such as human and the like through the skin is preferable.

Specific examples of such drug include general anesthetics, hypnotic sedatives, antiepileptic drugs, antipyretic analgesic antiphlogistic drugs, anti-vertiginous drugs, psychoneurotic drugs, topical anesthetics, skeleton muscle relaxants, autonomic drugs, antispasmodic drugs, anti-parkinsonian drugs, anti-histamine drugs, cardiac stimulants, drugs for arrhythmia, diuretic, hypotensive drug, vasoconstrictor, coronary vasodilator, peripheral vasodilators, arteriosclerosis drugs, drugs for circulatory organ, anapnoics, antitussive expectorant, hormone drugs, external drugs for purulent diseases, analgesic-antipruritic-styptic-anti-inflammatory agent drugs, drugs for parasitic skin diseases, hemostatic drugs, gout treatment drugs, drugs for diabetes, antimalignant tumor agents, antibiotic, chemical therapy agents, narcotic, quit smoking aids and the like.

While the content of the drug is not particularly limited as long as it can afford an effect by transdermal absorption and does not impair adhesion property of the adhesive, it is preferably 0.1-60 wt %, more preferably 0.1-40 wt %. When the content is not less than 0.1 wt %, a sufficient treatment effect can be obtained. When the content is not more than 60 wt %, the possibility of developing skin irritation is eliminated and economic advantage can also be afforded.

When desired, the adhesive layer can contain an organic liquid component. The organic liquid component is not particularly limited, and examples thereof include glycols such as ethylene glycol, diethylene glycol, propylene glycol, dipropylene glycol, tripropylene glycol, triethylene glycol, poly(ethylene glycol), poly(propylene glycol) and the like; fats and oils such as olive oil, castor oil and the like; lanolin; hydrocarbons such as squalane and liquid paraffin; various surfactants; ethoxylated stearyl alcohol; glycerol monoesters such as oleic acid monoglyceride, caprylic acid monoglyceride and lauryl acid monoglyceride; dialkyl ester of polyalkylene glycol such as poly(propylene glycol); glycerol diester such as glycerol diacetate and the like, glycerol triester such as glycerol triacetate and the like, or a mixture thereof; fatty acid alkyl ester such as triethyl citrate and the like; long chain alcohol; higher fatty acid such as oleic acid and caprylic acid; alkyl ester of higher fatty acid such as isopropyl myristate; pyrrolidones such as N-methylpyrrolidone and N-dodecylpyrrolidone; sulfoxides such as decyl methyl sulfoxide; 1,3-butanediol and the like. These can be used alone or in a mixture of two or more kinds thereof.

The content of the organic liquid component is preferably 10-60 wt, more preferably 15-60 wt %, most preferably 20-60 wt %. When the content of the component is not less than 10 wt %, the adhesive layer is easily plasticized, and adhesive layer components are easily protruded or outflown from the edge of the adhesive layer. Therefore, the present invention capable of effectively suppressing such phenomenon is advantageous in such case. When the content of the organic liquid component exceeds 60 wt %, the adhesive layer may face difficulty in retaining a given shape.

A release liner to protect the adhesive surface can be laminated on the adhesive surface of the adhesive layer of the adhesive patch main part, before applying the adhesive patch main part to the skin. The release liner is not particularly limited, and examples of the material thereof include those known per se in the field. Specific examples thereof include plastic films of polyesters such as poly(ethylene terephthalate), poly(vinyl chloride), poly(vinylidene chloride), various acrylic-based and methacrylic-based polymers, polystyrene, polycarbonate, polyimide, acetyl cellulose, regenerated cellulose (cellophane), celluloid and the like, a laminate film of high-quality paper, glassine paper and the like and polyolefin and the like. For safety, economic efficiency and drug-transfer properties, a polyester film is preferably used.

The release liner is preferably treated for easy peeling on the interfacial surface side with an adhesive, so as to facilitate peeling from the adhesive layer. While the easy peeling treatment is not limited, a known method can be applied. For example, a treatment for forming a peeling-treated layer using a release agent comprising a curable silicone resin as a main component by a coating method such as bar coating, gravure coating and the like can be applied.

The thickness of the peeling-treated layer is preferably 0.01-5 μm to ensure release property and uniformity of the coating. The thickness of the release liner having a peeling-treated layer is generally 10-200 μm, preferably 50-100 μm, from the aspect of handling property.

As the production method of the adhesive patch and adhesive preparation as mentioned above, various methods are available. However, for industrial production, for example, the following method is preferable for high production efficiency.

A composition for formation of the central part adhesive layer is applied to a region of at least one surface of a release liner, which corresponds to the central part of the adhesive patch to be obtained later, and dried to give an adhesive layer substantially free of voids. Then a composition for formation of a peripheral part adhesive layer, which comprises air bubbles, is applied to a region corresponding to the peripheral part on the periphery of the formed adhesive layer and dried to give an adhesive layer containing voids. Such air bubbles can be introduced by stirring, aerating and/or bubbling a composition for formation of a peripheral part adhesive layer in the air before application. The size of the air bubbles can be adjusted by increasing or decreasing such stirring, aeration, and/or bubbling intensity and/or time. In a preferable embodiment of the present invention, the quantity of airflow is 100-10000 ml/min relative to 2500 g of a composition for formation of a peripheral part adhesive layer and the aeration time is several minutes to several dozen minutes. While the aeration method is not limited, for example, it can be performed by injecting or suctioning the gas via a porous material or one or more tubes. Finally, a support is laminated on the regions corresponding to the central part and the peripheral part of the adhesive layer thus formed to give an original sheet for adhesive patch production.

Alternatively, a composition for formation of the central part adhesive layer and a composition for formation of a peripheral part adhesive layer are similarly applied to at least one surface of a support and dried to give the adhesive layer. Then, a release liner is laminated thereon to give an original sheet for adhesive patch production.

A method for the above-mentioned lamination is not particularly limited, and a known means such as coating, adhesion, fusion bonding, melt-bonding, pressure bonding and the like of a primer and the like can be employed.

Next the original sheet for adhesive patch production (hereinafter to be also simply referred to as an original sheet) is punched out at a punching position of the outer circumference of the peripheral part to be formed, whereby an adhesive patch of the embodiment shown in FIG. 1 of the present invention can be obtained.

When an adhesive patch of the embodiment shown in FIG. 2 is to be produced, an original sheet is pressed to be stamped from the support side with a heated stamp having a given shape. The aforementioned predetermined shape is such a shape as presses at least an area corresponding to the peripheral part of the adhesive patch during pressing. After the stamping, the original sheet is punched out at a punching position of the outer circumference of the peripheral part to be formed, whereby an adhesive patch of the embodiment wherein the peripheral part of the adhesive layer has a thickness smaller than that of the central part of the adhesive layer can be obtained. While the shape of the heated stamp varies depending on the shape of the adhesive patch to be formed, for example, a flat plane shape defined by two rectangles on the same axis can be employed.

Here, use of a heated stamp is necessary. A heated stamp softens a support comprising a resin film adjacent to the pressed area with heat, which in turn releases the adhesive layer in the pressed area, and encourages formation of the area corresponding to the intermediate part. The adhesive patch main part corresponding to the once-formed intermediate part is later allowed to cool by slow cooling and the like and maintains its shape.

While the material of the stamp is not particularly limited, iron is preferable. Stainless steel may develop heat distortion and the processing thereof may be difficult. Aluminum and brass can be processed easily, but duration of the stamp may be inferior.

The punching means is not particularly limited, and laser, press-cutting blade and the like can be employed. Since adjustment of cutting size and position adjustment are easy and a clear end surface can be obtained, an original sheet is preferably punched out with a press-cutting blade dies set (male die and female die).

The release liner can be easily peeled off. By peeling off the release liner, the adhesive patch of the present invention comprising a support and an adhesive layer formed on at least one surface of the support can be obtained. The release liner can have a dividing line as necessary, which helps detach the release liner easily when in use of the adhesive patch.

EXEMPLARY EMBODIMENTS

The present invention is explained in more detail in the following by referring to Examples and Comparative Examples, which are not to be construed as limitative.

Examples 1 and 2

Preparation of Composition for Adhesive Layer Formation (1) Preparation of Composition for the Central Part Adhesive Layer Formation Toluene (625.0 g), n-hexane (875.0 g), high molecular weight polyisobutylene (viscosity average molecular weight 4,000,000, 104.3 g), medium molecular weight polyisobutylene (viscosity average molecular weight 55,000, 208.7 g), a tackifier (alicyclic saturated hydrocarbon resin, softening point 141° C. (ring and ball method), 208.7 g), and toluene (50.0 g) were separately weighed and mixed, and the mixture was stirred until it became uniform. Then, an organic liquid component (isopropyl myristate, 228.2 g) and toluene (200.0 g) were weighed and added to the aforementioned solution.

Similarly, the mixture was stirred until it became uniform to give a composition for formation of the central part adhesive layer.

(2) Preparation of Composition for Peripheral Part Adhesive Layer Formation

The composition (viscosity 25 Pa·s) was prepared in the same manner as for the composition for formation of the central part adhesive layer and air bubbles were introduced by blowing air through a tube (one) into the composition (2500 g) before coating at a rate of 1000 ml/min for 10 min.

Preparation of Original Sheet for Adhesive Patch Production

Figure 5B:
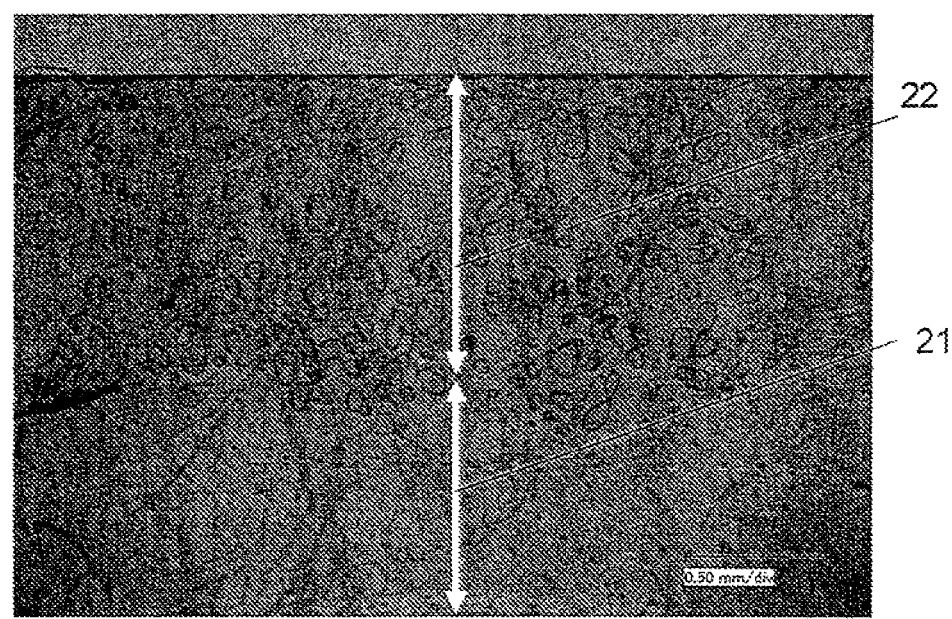
FIG. 5B shows the adhesive layer substantially free of voids, which is formed on the region corresponding to the central part of the adhesive patch and laminated on a release liner, a region adjacent thereto, which corresponds to the peripheral part of the adhesive patch and coated with a composition for formation of a peripheral part adhesive layer, as well as air bubbles in the region, all of which were taken by microscope VHX-500 manufactured by KEYENCE CORPORATION at 200-power.

A composition for formation of the central part adhesive layer was applied to a region of an easy-release surface of a release liner (thickness 75 μm) made from poly(ethylene terephthalate) (hereinafter to be also indicated as "PET"), which corresponded to the central part (56 mm×56 mm) of the adhesive patch to be obtained later, such that the thickness of the adhesive layer after drying was 160 μm, and dried in a drying machine (100° C.) to give a release liner having an adhesive layer substantially free of voids. Then, a composition for formation of a peripheral part adhesive layer was similarly applied to the periphery (width about 5 mm) of the adhesive layer (FIG. 5B shows the adhesive layer formed on the region corresponding to the central part of the adhesive patch, and air bubbles in a region corresponding to the peripheral part of the adhesive layer, all of which were taken by microscope VHX-500 manufactured by KEYENCE CORPORATION at 200-power). The coated composition for formation of a peripheral part adhesive layer was dried (100° C.), whereby a release liner having an adhesive layer (non-crosslinked) wherein voids are localized in the region corresponding to the peripheral part and the region corresponding to the central part is substantially free of voids was obtained. The surface where the adhesive layer had been formed was adhered to a PET non-woven fabric surface of a support, which is a laminate (total thickness 40 μm) of a 4.5 μm-thick PET film and a 35 μm-thick PET non-woven fabric (basis weight 20 g/m$^2$) by pressure bonding to give an original sheet for producing adhesive patch.

Production of Adhesive Patch

Using a heated stamp having a flat plane defined by two almost square shapes on the same axis, the support surface of the original sheet for adhesive patch punching was heated and pressed. An adhesive patch main part and a release liner were simultaneously punched out from the heated and pressed original sheet using a press-cutting blade dies set such that the heated and pressed area corresponded to the peripheral part of a adhesive patch to be obtained later, whereby the adhesive patch of the present invention was obtained. The obtained adhesive patch and the adhesive patch main part each had an about square outline of about 60 mm one side, and had a band-like peripheral part (width about 1.5 mm) in the whole outer circumference, an about square the central part inside the peripheral part, and a band-like intermediate part between the central part and the peripheral part. The adhesive patch was tightly sealed in a packaging material with an outer layer made of a 12 μm-thick PET film and an inner layer made of a 30 μm-thick polyacrylonitrile-based resin film to give an adhesive patch package having two V-shaped notches.

The obtained adhesive patch package was preserved at 25° C. for one month with a load of 3 g/cm$^2$ in the thickness direction of the package.

Example 3

An adhesive patch was produced in the same manner as in Examples 1 and 2 except that the region corresponding to the peripheral part of the adhesive patch was not heat-pressed by stamping, and an adhesive patch package was produced.

Comparative Example 1

An adhesive patch was produced in the same manner as in Examples 1 and 2 except that air bubbles were not introduced into a composition for formation of a peripheral part adhesive layer before coating of the composition and the region corresponding to the peripheral part of the adhesive patch was not heat-pressed by stamping, and an adhesive patch package was produced.

Comparative Example 2

An adhesive patch was produced in the same manner as in Examples 1 and 2 except that the amount of the air bubbles introduced into a composition for formation of the central part adhesive layer was decreased by blowing the air into the composition (2500 g) at 10 ml/min for 1 min after preparation of the composition, and an adhesive patch package was produced.

Experimental Example 1

Measurement of Average Number of Voids Contained in Adhesive Layer

An average number of voids was determined by producing a section perpendicular to the main surface of the adhesive patch with a freezing microtome (LR-85 manufactured by YAMATO KOHKI INDUSTRIAL CO., LTD.) at at least 4 points of the adhesive patch, imaging the section with an FE-SEM (Hitachi, field-emission-type scanning electron microscope S-4800) at 50- to 1000-power, and reading the gauge scale.

For each point, the patch was cut in both the central part and the peripheral part for at least 3000 μm, each section was imaged, counting, based on the gauge scale, voids having a diameter (maximum diameter) of not less than 1 μm in the thickness direction of an adhesive patch in a 700 μm×600 μm section of each image and an average number of voids per 1 mm$^3$ adhesive layer was calculated.

Even when one or more kinds of voids are partly connected, as long as they are not observed as being completely divided, the voids are counted as one. The voids in the observed section, which have a diameter (maximum diameter) of not less than 1 μm in the thickness direction of an adhesive patch, were observed.

Experimental Example 2

Measurement of Thickness of Adhesive Layer

The adhesive patch was stained with aqueous ruthenium acid solution, sectioned in the direction perpendicular to the main surface of the adhesive patch with a freezing microtome (same as above), and the section was observed and photographed with FE-SEM (Hitachi, field-emission-type scanning electron microscope S-4800) at 50- to 1000-power.

The gauge scales of the peripheral part and the central part were read, whereby the thicknesses of the PET film and the PET non-woven fabric, and the thickness (total of thickness of adhesive layer and thickness of support) of the adhesive patch main part were measured. In this case, concaves and convexes are present on the surface of the PET non-woven fabric. In a sectional image, 10 convexes are selected at random, and an average of the thickness of the PET non-woven fabric at the convexes was calculated and taken as the thickness of the PET non-woven fabric. Then, the thickness of the PET film and the thickness of the aforementioned PET non-woven fabric were subtracted from the thickness of the adhesive patch main part, and the thicknesses of the adhesive layer at the peripheral part and the central part were determined.

Experimental Example 3

Evaluation of Take Out Performance of Adhesive Patch from Package

Figure 6A:
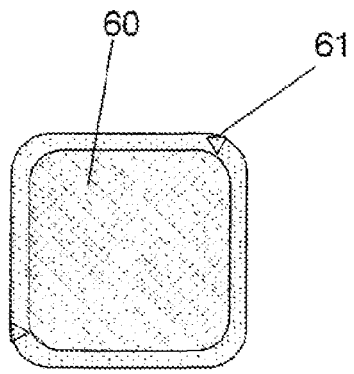
FIGS. 6A-6D show that an adhesive patch package is opened by cutting two sides with scissors or along a V-shaped notch, and the adhesive patch is taken out.
Figure 6B:
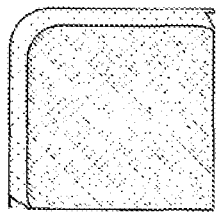
Figure 6C:
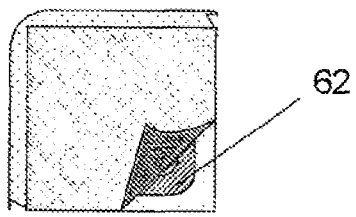
Figure 6D:
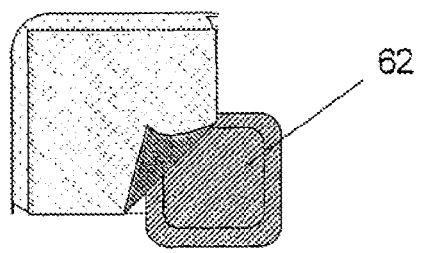

Using an adhesive patch immediately after production and an adhesive patch after preservation at 25° C. for one month, as shown in FIGS. 6A-6D, two sides of the package 60 (FIG. 6A) containing an adhesive patch 62 were opened with scissors or manually opened along V-shaped notch 61 (FIG. 6B). The package was broken away from an unsealed part (FIG. 6C), the adhesive patch 62 was taken out from the package 60 while holding a corner thereof (FIG. 6D), and the take out performance of the adhesive patch from the package was evaluated using 1-5 scores based on the following evaluation criteria.
<Evaluation Criteria>
5: can be taken out extremely easily with no protrusion of the adhesive layer
4: can be taken out extremely easily though the adhesive layer protrudes slightly
3: can be taken out easily though the adhesive layer protrudes somewhat
2: can be taken out though the adhesive layer protrudes somewhat
1: cannot be taken out easily since the adhesive layer protrudes considerably Experimental Example 4

Evaluation of Skin Adhesion Performance

Using an adhesive patch immediately after production and an adhesive patch after preservation at 25° C. for one month, a specialized estimator took out an adhesive patch from a package, adhered the patch to the chest for 24 hr from the morning, and evaluated the adhesion state using 1-5 scores based on the following evaluation criteria. During adhesion, the estimator behaved as usual. When the estimator took a bath in the morning, the patch was adhered avoiding immediately after taking a bath (within 30 min). The same one estimator evaluated each Example and Comparative Example once.
<Evaluation Criteria>
5: adhesion of adhesive patch to the skin is maintained fine and the edge of adhesive patch does not turn up
4: adhesion of adhesive patch to the skin is maintained fine but the edge of adhesive patch slightly turns up
3: adhesion of adhesive patch to the skin is maintained fine but the edge of adhesive patch turns up in some parts
2: adhesion of adhesive patch to the skin is maintained but adhesiveness decreases as compared to initial stage of adhesion and the edge of adhesive patch turns up in some parts
1: adhesive patch falls off The evaluation results are shown in Table 1. In Table 1, the "average number of voids" shows an average number of voids contained in the adhesive layer (average number of voids contained per unit volume of the adhesive layer).

TABLE 1

| | average number of voids (voids/mm$^3$) | | thickness (μm) of adhesive layer | | take out performance from package | | skin adhesion performance | |
|---|---|---|---|---|---|---|---|---|
| | central part | peripheral part | central part | peripheral part | immediately after production | after preservation | immediately after production | after preservation |
| Comp. Ex. 1 | 0 | 0 | 250 | 250 | 3 | 1 | 4 | 3 |
| Ex. 1 | 0 | 8 | 250 | 80 | 5 | 5 | 5 | 5 |
| Ex. 2 | 0 | 3 | 250 | 30 | 5 | 5 | 5 | 4 |
| Ex. 3 | 0 | 20 | 250 | 250 | 4 | 2 | 4 | 3 |
| Comp. Ex. 2 | 0 | 1 | 250 | 80 | 3 | 1 | 4 | 3 |

As shown in Table 1, the adhesive patches of Examples 1 to 3 were free of voids in the central part of the adhesive layer, and the peripheral part of the adhesive layer contained voids at 3-20 voids/mm$^3$ on average. The adhesive patch of Example 2 had voids penetrating from the release liner to the support in the peripheral part of the adhesive layer and other Examples and Comparative Examples were free of such voids. Such adhesive patches of Examples 1 to 3 were found to show superior take out performance from the package and superior skin adhesion performance. In Comparative Example 1 where the peripheral part of the adhesive layer is free of voids, and Comparative Example 2 where the peripheral part of the adhesive layer contains voids at 1 void/mm$^3$ on average, the take out performance from the package and skin adhesion performance were inferior.

The adhesive patch of the present invention can be preferably used as a medical adhesive patch to cover and protect affected parts on the skin surface. When a drug is contained, it can be used as an adhesive preparation for continuous transdermal administration of a transdermally absorbable drug.

This application is based on a patent application No. 2008-219190 filed in Japan, the contents of which are incorporated in full herein by this reference.

What is claimed is:
1. An adhesive patch, comprising:
an impermeable support having opposite sides;
an adhesive layer formed on a surface of one of said sides of said support;

wherein said adhesive patch has a central part and a peripheral part and said adhesive layer is formed on said surface of said one of said sides of said support at both said central part and said peripheral part of said adhesive patch;

wherein said adhesive layer has voids therein;

wherein said adhesive layer, in said central part of said adhesive patch, is substantially free of said voids; and wherein said adhesive layer, in said peripheral part of said adhesive patch, has said voids localized therein.

2. The adhesive patch of claim 1, wherein said adhesive layer, in said peripheral part of said adhesive patch, has voids at an average rate of 2.0-100 voids per cubic millimeter.

3. The adhesive patch of claim 1, wherein said adhesive layer, in said peripheral part of said adhesive patch, has a thickness smaller than that of said adhesive layer in said central part of said adhesive patch.

4. The adhesive patch of claim 1, wherein said support comprises a laminate of a porous material and a resin film, with said adhesive layer being laminated on said porous material.

5. The adhesive patch of claim 1, wherein said peripheral part of said adhesive patch has a flat plane shape and comprises a band-like portion that surrounds said central part, said band-like portion having a width of 0.29-3.5 mm.

6. The adhesive patch of claim 1, wherein said adhesive layer, in said central part of said adhesive patch, has a thickness of not less than 50 micrometers.

7. The adhesive patch of claim 1, wherein said adhesive layer, in said central part of said adhesive patch, has a thickness of 100-4000 micrometers and said adhesive layer, in said peripheral part of said adhesive patch, has a thickness of 1.5-300 micrometers, wherein said adhesive layer, in said peripheral part of said adhesive patch, has a smaller thickness than said adhesive layer in said peripheral part of said adhesive patch.

8. The adhesive patch of claim 1, wherein said adhesive layer further comprises a drug.

9. The adhesive patch of claim 1, and further comprising a release liner laminated on said adhesive layer.

10. The adhesive patch of claim 1, wherein said support is formed such that, as seen in a direction perpendicular to a plane of said adhesive layer on a side of said adhesive layer facing away from said surface on said support on which said adhesive layer is formed, any line connecting one point along an edge of said support with an other point along the edge of said support lies completely within the edges of said support.

* * * * *